United States Patent [19]

Wood

[11] Patent Number: 4,716,123

[45] Date of Patent: Dec. 29, 1987

[54] SOLID PHASE BIOLOGICAL DIAGNOSTIC ASSAY VIA VISUAL OBSERVATION AS ENHANCED BY MIE SCATTERING

[75] Inventor: David E. Wood, Chelsea, Mich.

[73] Assignee: Covalent Technology Corporation, Ann Arbor, Mich.

[21] Appl. No.: 898,874

[22] Filed: Aug. 20, 1986

Related U.S. Application Data

[63] Continuation of Ser. No. 501,268, Jun. 6, 1983, abandoned, which is a continuation-in-part of Ser. No. 469,939, Feb. 25, 1983, abandoned, which is a continuation-in-part of Ser. No. 224,984, Jan. 14, 1981, abandoned.

[51] Int. Cl.[4] .......... G01N 33/546

[52] U.S. Cl. .......... 436/533; 422/56; 422/57; 435/4; 435/7; 435/805; 435/810; 436/531; 436/532; 436/534; 436/536; 436/805

[58] Field of Search .......... 435/4, 7, 805, 810; 436/531-534, 536, 805; 422/56, 57

[56] References Cited

U.S. PATENT DOCUMENTS

| | | | |
|---|---|---|---|
| 3,770,380 | 11/1973 | Smith | 422/57 |
| 4,169,138 | 9/1979 | Jonsson | 422/57 |
| 4,256,725 | 3/1981 | Rutner | 436/810 |
| 4,279,993 | 7/1981 | Magers et al. | 436/805 |
| 4,293,538 | 10/1981 | McAleer et al. | 436/810 |
| 4,305,924 | 12/1981 | Piasio et al. | 436/810 |
| 4,378,344 | 3/1983 | Zahradnik et al. | 436/810 |

FOREIGN PATENT DOCUMENTS 0070527 1/1983 European Pat. Off. .

OTHER PUBLICATIONS

Bernard et al.—Clinical Chemistry, vol. 27 (1981), pp. 832-837.

Quash et al.—J. Immunol. Methods, vol. 22 (1978), pp. 165-174.

Grange et al.—J. Immunol. Methods, vol. 18 (1977), pp. 365-375.

*Primary Examiner*—Sam Rosen

*Attorney, Agent, or Firm*—Fliesler, Dubb, Meyer & Lovejoy

[57] ABSTRACT

Methods and kits are set out having improved selectivity and improved sensitivity for use in field and home immunoassays. A specifically binding biomaterial is attached to a macroextensive surface of a plastic strip or the like. A biological substance which is a specific binding partner to a binding site of the specifically binding biomaterial is attached to each of a plurality of synthetic particles. The particles are of a preselected size, refractive index, or the like to enhance their visibility in accordance with the Mie scattering phenomenon. Testing is by either contacting the particles with the strips to obtain adherence of the particles to the strips, or by exposing strips having the particles already adhering to them to a solution containing either the specifically binding biomaterial or the biological substance, whereby the particles adherence to the strip is eliminated. A quick and accurate pregnancy test is one result of the invention.

45 Claims, 5 Drawing Figures

SOLID PHASE BIOLOGICAL DIAGNOSTIC ASSAY VIA VISUAL OBSERVATION AS ENHANCED BY MIE SCATTERING

CROSS-REFERENCE

This application is a continuation of U.S. patent application Ser. No. 501,268, filed June 6, 1983, now abandoned, which is a continuation-in-part of U.S. patent application Ser. No. 469,939, filed Feb. 25, 1983, now abandoned, which is a continuation-in-part of now abandoned U.S. patent application Ser. No. 224,984, filed Jan. 14, 1981.

TECHNICAL FIELD

This invention relates to a method for assaying aqueous samples for specific biological or immunological substances.

BACKGROUND ART

Soluble biological substances attached to carriers have many uses in diagnostic tests, enzyme processes, and affinity purifications. For example, attachment of antibodies or antigens to a carrier allows their immunological partners to be easily removed from a mixture of many substances. Similarly, attaching enzymes to a carrier allows them to be easily removed from a reaction mixture or to be used in a continuous flow process. Heterogeneous radioimmunoassays and enzyme immunoassays rely on attachment of one or more of the reactants to a solid phase to enable separation from the free reactants. Agglutination assays (to determine the presence of an antigen or an antibody in a fluid) utilize indicator or carrier particles (on which are carried the appropriate immunological material) in order to make the immunological complex more easily visible. Separation and identification of cells, cellular constituents, and bacteria are aided by antibodies or antigens coupled to solids. Biological particles will, for example, specifically adhere to solids coated with appropriate antibodies and antigens so that separation from other particles can be affected. Identification of biological particles can be made through the specific adherence of small particles coated with appropriate antibody or antigen. These small particles can incorporate a substance such as a fluorescent dye, radioactive tracer, or electron dense substance which make their presence more readily detectable.

The currently available simple procedures for bioactive material testing, for field test methods (e.g., over the counter pregnancy test kits, rely primarily on agglutination reactions or on enzyme catalyzed color reactions. These procedures use one of several core materials in their reaction, i.e., they use sheep's red blood cells, latex particles, or killed Staphylococcus cells as carriers. Such procedures are quite fast, usually taking less than an hour to complete. However, such procedures have several significant drawbacks. First, the biological core materials, when utilized, have production difficulties that can lead to non-reproducible test results for specific bioactive materials. Second, the maximum sensitivity level for reproducible, reliable results, is in the microgram per milliliter concentration range. This is far above the 1-10 nanogram per milliliter sensitivity which is required for early hormonal, viral or bacteriological analyte detection.

The agglutination procedures often require the careful manipulation of two solutions so that a successful reaction will occur to cause agglutination. Manipulations usually take the form of stirring small volumes of the solution on a specially designed flat surface and then waiting for the agglutinates to appear, or mixing two solutions by rocking a specially designed flat surface back and forth steadily until agglutinates appear. In another form of common agglutination test two regents are mixed in a test tube. As the agglutinate forms, it becomes insoluble and precipitates out to form a pattern on the tube bottom. This is observed and is accorded a negative or positive classification by its shape. The appearance of the agglutination reaction is in no way standardized and is therefore easily misinterpreted by persons with inadequate training or instruction. The agglutination procedures are very technique dependent. Generally it requires about two hours of training to qualify an operator already familiar with laboratory techniques to carry out the slide-type test. When the agglutination procedure is carried out in a test tube as described above, it is extremely sensitive to vibration, temperature changes and mixing techniques.

The enzyme catalyzed reaction of the prior art require preparation of biological substrates for the enzymatic reaction and careful manipulation of several reagent substances to first start the reaction and then, after a rather precise time interval, to stop the reaction before an observation can be completed. The enzyme test procedures are sensitive to temperature changes. During the reaction incubation the ambient temperature must be assumed to be about 22° C. The reactions are very difficult to stop, sometimes requiring the use of strong bases, e.g., 10 N sodium hydroxide for this purpose. And, they are quite time dependent. That is, they are kinetic reactions that must be closely timed for accurate and precise test results.

The prior art field tests, or home use tests, for bioactive materials thus have a number of very serious problems.

DISCLOSURE OF INVENTION

The present invention is directed to overcoming one or more of the problems as set forth above.

In accordance with one embodiment of the present invention, a method is set out for assaying an aqueous sample containing a specifically binding biomaterial having a binding site which is a specific binding partner to a biological substance, the specifically binding biomaterial being in association with other biomaterials, with increased speed, ease of assaying, specificity and sensitivity. The method comprises contacting a synthetic polymeric solid support haying a water insoluble macroextensive surface capable of associating with the specifically binding biomaterial and with the aqueous sample for a time sufficient for the specifically binding biomaterial to associate with the surface. The support is separated from contact with the aqueous sample. The separated surface is contacted with an aqueous solution containing a plurality of particles having particle surfaces bearing the biological substance associated therewith for a time sufficient for the binding site to bind to the biological substance and to thereby bind the particles to the surface. The support is separated from the aqueous solution and rinsed to remove any non-bound particles. The degree of adherence of the particles to the surface is observed.

In accordance with another aspect of the present invention a method is set out for assaying an aqueous sample containing a quantity of a specifically binding biomaterial having a binding site which is a specific binding partner to a biological substance, the specifically binding biomaterial being in association with other biomaterials, with increased speed, ease of assaying, specificity and sensitivity. The method comprises contacting the aqueous sample with a solid support having a water insoluble macroextensive surface associated with a selected one of the specifically binding biomaterial and the biological substance, the solid support having bound thereto a plurality of particles having particle surfaces associated with a selected other of the specifically binding biomaterial and the biological substance, the binding of the particles to the surface being via binding of the biological substance to the binding sites. The degree of release of the particles from the surface is then observed.

In accordance with still another embodiment of the present invention a kit is provided for assaying an aqueous sample containing a quantity of a specifically binding biomaterial having a binding site which is a specific binding partner to a biological substance, said specifically binding biomaterial being in association with other biomaterials, with increased speed, ease of assaying, specificity and sensitivity. The kit comprises a solid support having a water insoluble synthetic polymeric macroextensive surface capable of associating with the specifically binding biomaterial and a plurality of particles having particle surfaces bearing the biological substance associated therewith.

In accordance with yet another aspect of the present invention a test kit is provided in the nature of a solid support having a water insoluble macroextensive surface associated with a selected one of a specifically binding biomaterial and a biological substance which is a specific binding partner to a binding site on the specifically binding biomaterial. The solid support has bound thereto a plurality of particles having particle surfaces associated with a selected other of the specifically binding biomaterial and the biological substance, the binding of the particles to the surface being via binding of the biological substance to the binding sites.

When operating in accordance with the various embodiments of the present invention, field or home tests for biomaterials can be performed accurately by an untrained person who simply reads some accompanying instructions. The test can not only be performed quickly, it can be performed easily and with great specificity and increased sensitivity over prior art tests. The methods and kits of the present invention are not sensitive to vibration and can be very easily interpreted by an untrained user. Because of the increased sensitivity of the test, the biomaterial can be determined in very low concentrations. For example, pregnancy testing (for human chorionic gonadotrophin (hCG)) can be accurately carried out before a period is missed. Furthermore, the timing during the incubation of the macroextensive surface with the aqueous sample is not at all critical. And, the test components can be moved during the reaction steps with no adverse effects on the test results. Still further, in accordance with certain aspects of the invention the macroextensive surface, with the analyte and particles bound thereto, can be washed and thereafter dried and stored to give a permanent record of the test results.

BRIEF DESCRIPTION OF THE DRAWINGS

The invention will be better understood by reference to the figures of the drawings wherein.

BEST MODE FOR CARRYING OUT THE INVENTION

Figure 1:
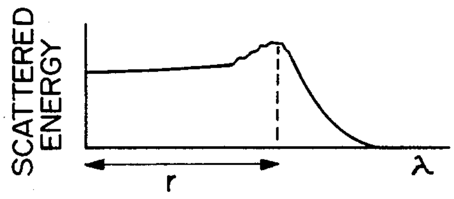
FIG. 1 illustrates, graphically scattering phenomenon as a function of wavelength.

In accordance with one aspect of the present invention a method is provided for assaying an aqueous sample containing a specifically binding biomaterial having a binding site which is a specific binding partner to a biological substance when the specifically binding biomaterial is in association with other biomaterials. The term "biomaterial" is used broadly to indicate any substance which is biologically active. The term "biological substance" is used broadly to indicate any substance which is a specific binding partner to a specific biomaterial. Illustrative of the biomaterials and of the biological substances are enzymes, antibodies, hormones, natural receptors, e.g., thyroxine binding globulin and avidin, globins, e.g., hemoglobin, ocular lens proteins, surface antigens, histo-compatibility antigens, and the like. The specifically binding biomaterial and the biological substance can be any such materials which are linkable to either a water insoluble support or a plurality of particles. A long list of such substances appears in U.S. Patent No. 4,264,766, issued Apr. 28, 1981.

The method and kit of the present invention utilize a water insoluble synthetic polymeric support having a macroextensive surface having the capability of associating with the specifically binding biomaterial. The solid support must be macroextensive and must define a macroextensive surface. For example, the solid support may be in the form of a strip of a suitable size for dipping into an aqueous sample and for being viewed. The strip may be of any convenient size, for example 2 to 10 millimeters wide by 30 to 80 millimeters long by perhaps 0.3 to 1 millimeter in thickness. The macroextensive surface will generally be hydrophobic thus giving it the ability to adsorb hydrophobic molecules such as the specifically binding biomaterial and other biomaterials. In some instances it may bear a biological substance which is a specific binding partner to the specifically binding biomaterial.

The solid support itself must be inert with respect to immunological diagnostic tests. A large number of materials can be used as the water insoluble support. Of particular interest are latexes as described in U.S. Pat. Nos. 4,046,723; 4,118,349; 4,140,662 and 4,264,766. Other useful polymers may be found in U.S. Pat. Nos. 3,619,371; 3,700,609; 3,853,987; 4,108,972 and 4,201,763. The polymer or latex supports can have active groups such as carboxyl groups, amine groups or groups convertible into them. Such is not, however, necessary. Polyvinylchloride is one particularly preferred material for the support. Another particularly preferred material for the support is polystyrene. The polystyrene may contain copolymerized therewith a carboxyl containing compound such as acrylic acid, methacrylic acid, or the like.

The particles of the present invention may be made of a like material as the support. That is, the latexes, polymers, and the like which can serve as the support can also serve as the particles. However, the particles are not so limited. Indeed, the particles can be in the nature of cells, including blood cells, yeast cells and bacterial cells having the biological substance attached to their membranes. The exact nature of the particles is thus, not critical if they are of a preselected size and refractive index. If the particles are polymeric in nature it is desired that the polymers be hydrophobic so that the biological substance can be adsorbed thereon.

For easy observation of sticking of the particles to the solid support it is desired that they be of a size so as to provide a clear visual clouding appearance on the solid support, which would in such instance preferably be transparent. It has been found that if the particles are selected to have an average diameter which falls about the range of the wavelength of visible light, i.e., from about 0.2 micron to about 2.0 microns, the clouding effect in air will be enhanced thus making visual observation of sticking of the particles to the transparent solid support clearer. In water the clouding effect is enhanced when the particles have an average particle diameter between about 0.47 and about 11.1 microns.

The visibility of a microsphere when viewed in visible light depends upon many factors: the size, the refractive index, the color, and the conductivity of the sphere. The most easily visible case, that is where the smallest quantity of material can be detected by its effect on light, excluding the case of fluorescence, is when the sphere resonantly scatters the light. This phenomenon was first explained in a paper published in 1908 by G. Mie, Ann. d. Physik, Volume 25 (1908), page 377. Mie presented his theory giving the rigorous solution for the scattering of a plane monochromatic wave by a homogenous sphere of any diameter and of any composition situated in a homogenous medium. The scattering that Mie described is commonly called Mie scattering. Mie scattering occurs when the size of the scattering particle is in the same range as the wavelength of the light being scattered. The scattering is strongly directed in a forward direction, that is, in a narrow cone with its apex at the center of the particle, in the same direction as the incident light. Other discussions of such scattering may be found in Light Scattering by Small Particles, H. C. Van de Hulst, John Wiley & Sons, Inc., New York, 1957; Principles of Optics, M. Born and E. Wolf, J. Springer, Berlin, 1933 and Particle Clouds, Dusts, Smokes and Mists, H. L. Green and W. R. Lane, E. & F. N. Spoon, Ltd., London, 1957.

A bit of basics first: A parallel beam of light traversing empty space is not attenuated. When one places an object or objects in the beam of light, the beam is attenuated. The term extinction is used for a quantitative measure of this reduction in the intensity of the light in the beam. The extinction generally consists of two parts: the scattering part and the absorbtion part. For the present purposes, only the effect of the former on the light beam will be considered. FIG. 1 shows the energy that is scattered out of a light beam by a particle of radius r as a function of the wavelength of the incident light. For light of wavelength much less than the radius of the particles doing the scattering, the scattered energy is nearly independent of the wavelength. For wavelengths much longer than the radius of the particles, the scattered energy falls off as the inverse fourth power of the wavelength. This latter is called Rayleigh scattering. The Rayleigh scattering follows a $1+\cos^2\theta$ dependence so that the light scattered at 90° to the incident beam has one-half of the intensity of the light scattered in the forward direction or in the reverse direction.

Figure 2:
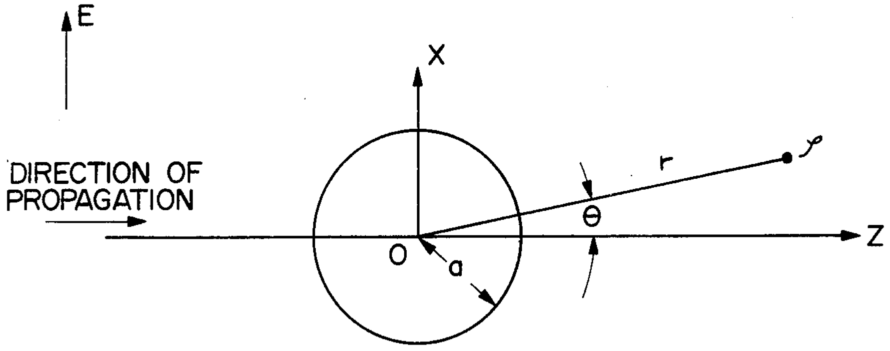
FIG. 2 illustrates, graphically, scattering by a sphere.
Figure 3:
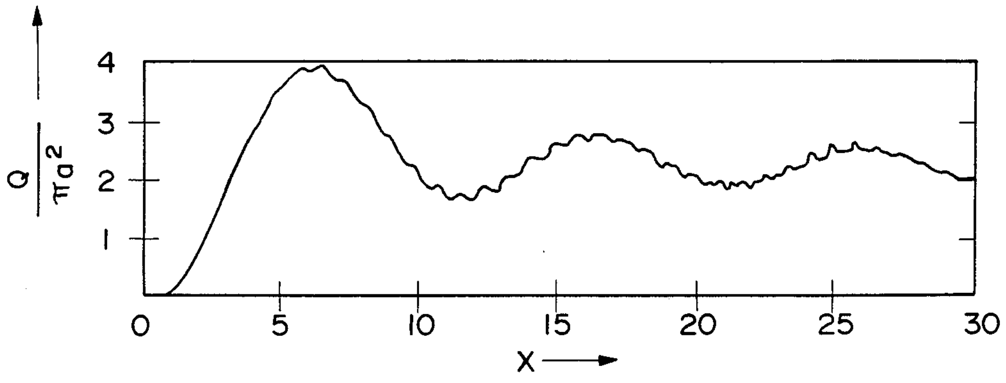
FIG. 3 illustrates, graphically, the scattering cross-section of dielectric spheres with 1.33 refractive index in air.

For the case where the diameter of the particles and the wavelength are nearly the same, the scattered energy is at maximum. This is the region of Mie scattering. FIG. 2 shows the coordinate system which defines the angle $\theta$ through which the light is scattered. The calculation of Mie scattering is rather complicated but results have been obtained for several systems and are easy to understand in a general way. FIG. 3 shows the scattering cross-section, Q, for dielectric spheres of refractive index 1.33 as a function of the parameter $x=(2\pi a)/\lambda$. Where "a" is the radius of the sphere and $\lambda$ is the wavelength of light, this corresponds to the scattering in air by droplets of water, for example, which have this refractive index. The first maximum in the scattering peak occurs near an "x" value of 6.0. The second maximum occurs at an "x" value of about 16. For a fixed radius "a", then, the "x" value plotted can be considered to be a plot of $1/\lambda$ (wavelength). Therefore, the extreme left of the diagram, where the wavelength is very large compared to the size of the particle, corresponds to the Rayleigh scattering regime: the intensity falls off as the inverse fourth power of the wavelength. As one goes well past the right hand end of the diagram, the oscillating curve asymptotically approaches the value of 2. This corresponds to the fact that the light is scattered out of the parallel beam by two effects: (1) the geometric blocking of the light by the cross-sectional area of the sphere and (2) the edge effect, which results in Fraunhofer diffraction. This latter produces another factor of 1.0 in the cross-section for scattering particles.

The meaning of the scattering cross-section, in this case with a maximum value of 4 for $x=6$, is that the light scattered out of a beam of wavelength $\lambda$ by a spherical particle of radius "a" and an index of refraction of 1.33, where $6=(2\pi a)/\lambda$, is equal to 4 times the cross-sectional area ($\pi a^2$) of that particle times the incident light intensity.

Figure 4:
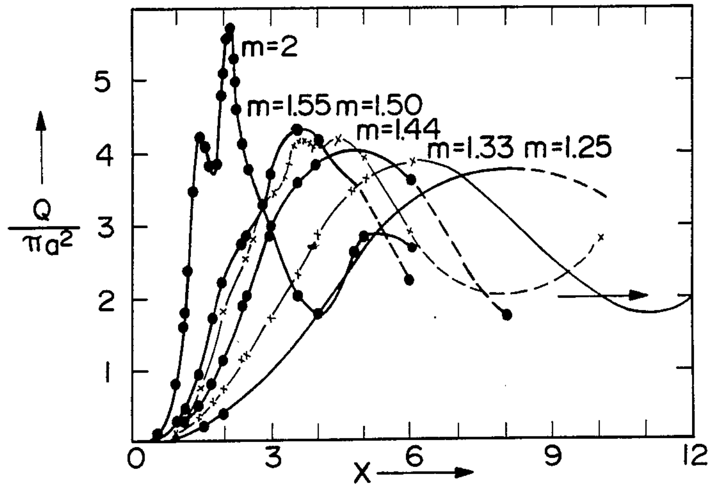
FIG. 4 illustrates, graphically, extinction curves for spheres of six different refractive indexes.
Figure 5:
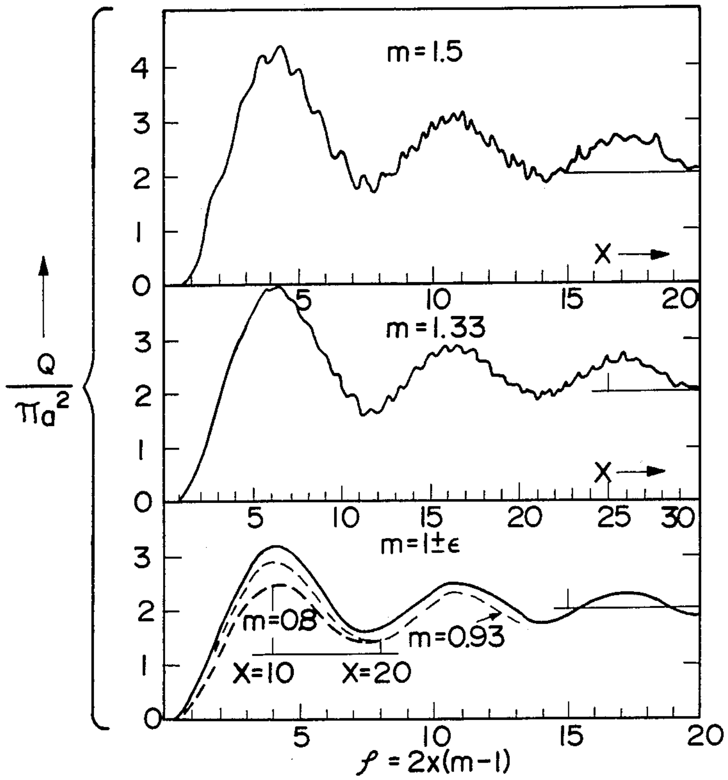
FIG. 5 illustrates, graphically, extinction curves calculated from Mie's formula.

FIG. 4 shows the extinction curves for spheres with different values of refractive index (m). It is seen that the maximum obtained value of Q increases slightly as the refractive index is increased. The curves indicate that the wavelength for the phenomenon of Mie scattering is dependent upon the refractive index of the particle. If, however, one plots the scattering cross-section as a function of the parameter $\rho=2x\,|m-1|$ one obtains curves that are extremely similar and in fact essentially superimposable if one neglects the minor wiggles. This is shown in FIG. 5. These curves in FIG. 5 are only accurate for index of refraction less than about 1.6, which covers almost any transparent material. The extra bump associated with the index of refraction of 2.0 in FIG. 4 corresponds to an optical resonance in the particle itself. As a generalization, the scattering curves in FIG. 5 are all calculated for particles in vacuum. If one is working with particles in a medium with refractive index other than 1.0 the difference in refractive index between the particles and the medium must be used as the refractive index for calculating the Mie scattering.

For large values of $\rho$ the maxima occur at $\rho=(k+\frac{3}{4})2\pi$ and the minima at $\rho=(k+\frac{1}{4})2\pi$, where k is an integer. For a refractive index very near to 1.0 the first maximum occurs at $\rho=4.09$, for a refractive index of 1.5 the first maximum occurs at $\rho=4.2$, and for a refractive index of 2.0 the first maximum occurs at $\rho=4.4$. For particles such as polystyrene microspheres, having an index of refraction of about 1.59, the first maximum for a 0.7 micron diameter sphere should occur at 620 nanometers which corresponds to red light. This behavior has been confirmed experimentally.

Table 1 shows some experimental results obtained using an antibody which detects the β-subunit of hCG. The number of spheres per square millimeter attached to the surface at the end of the test is shown in column 1. The fractional area covered by these 0.7 micron diameter spheres is shown in column 2. The theoretical scattering is shown in column 3. This theoretical scattering allows for scattering by the particles on both sides of the thin plastic strip that was used. The scattering expected from the 1.0 nanogram per milliliter sample is thus about four times background scattering from the negative sample and is easily observed by placing the strip in a beam of light and observing the light scattered from the microspheres on the strip. This test was done with an antibody which was specific to the detached β-subunit of HCG. Therefore, the results for the pregnancy urine of 4.4% corresponds to only about 1% of the total HCG expected in pregnancy urine. Use of an antibody to the intact hCG molecule does result in much larger binding of microspheres to the plastic strips for pregnancy urine. Experiments in which strips were artificially coated with microspheres to higher levels gave the expected results. For example, a strip coated with fractional area 0.084 on each side is expected to scatter 67% of the light out of the incident beam. It was obvious by eye that this was the approximate level of scattering that such a strip did exhibit.

TABLE I

| HCG in test urine | Spheres/ $mm^2$ | Fractional Area Covered Per Side | Theoretical Scattering (Total Both Sides) |
|---|---|---|---|
| negative | 4,500 | .0017 | 1.3% |
| 1.0 ngm/ml | 17,000 | .0063 | 5.0% |
| 10.0 ngms/ml | 30,000 | .0113 | 9.1% |
| pregnancy | 15,000 | .0055 | 4.4% |

All of the foregoing has concerned spherical particles which do not absorb light. The effect of including an absorber in the particle is to dampen the oscillation (lower the peaks and raise the valleys) and ultimately shift the curve to lower wavelength can either reduce the scattering cross-section or increase it, depending on the position of the absorbing line relative to the peaks and valleys of the Mie scattering for that particle.

The equation for finding maxima and minima is $$\frac{2a}{\lambda} = \frac{\rho}{2|m-1|}$$

The particles of interest (plastics, cells, etc.) have an index of refraction m in the range from 1.4 to 1.6. For m in this range, with air as the medium, the maximum occurs at $\rho=4.2$. Therefore, $(2a)/\lambda$, at maximum scattering, varies from 1.67 to 1.11.

For light of visible wavelength, $\lambda=0.4$ micron to 0.7 micron, 2a varies from 0.4 micron to 1.2 microns (using maximum and minimum products).

Looking at FIG. 5 one can see that the maximum scattering falls off by at least half by $\rho=2.0$ and by $\rho=7.0$, so we extend the size range to these values and get >0.2 micron to 2.0 micron diameter as the appropriate preferred range for particles in an air medium.

For particles in water (refractive index=1.33) $|m-1.33|$ should be used in place of $|m-1|$. Therefore, $|m-1.33|$ varies from 0.07 to 0.27 and for particles in this range the maximum occurs at $\rho=4.09$. Therefore, $(2a)/\lambda$ at maximum scattering varies from 9.3 to 2.4. As before, for $\lambda=0.4$ micron to 0.7 micron, 2a varies from 0.96 micron to 6.5 microns. Again picking $\rho=2.0$ and $\rho=7.0$ as outer limits one gets >0.47 micron to 11.1 microns diameter as the appropriate range for particles in a water medium.

To summarize, particles will be more easily visually detected in air if their average diameters are between about 0.2 and 2.0 microns, more preferably between about 0.4 and 1.2 microns. In water these ranges are changed to between about 0.47 and 11.1 microns and 0.96 and 6.5 microns, respectively.

It is also possible to add a color imparting agent to the particles so as to make clearer the observation of sticking of particles to a solid support which may or may not be transparent. Fluorescing agents or other tracers can also be added to the particles, if desired, although a major advantage of the test is that such are not required.

In accordance with the present invention the solid support as just described is contacted with an aqueous sample for a time sufficient for the specifically binding biomaterial to associate with the macroextensive surface of the support. This can be accomplished, for example, by simply placing a strip of plastic, for example polyvinylchloride plastic, in a sample such as the urine of a woman suspected of being pregnant. The macroextensive surface will then adsorb not only the specific binding biomaterial but other biomaterials as well. In this case, the specifically binding biomaterial might be β-hCG. The strip would then be separated from contact with the aqueous sample as by removing it from the urine sample. Usually the surface would then be rinsed off, for example with phosphate buffered saline.

In those instances wherein the strip has not been in any way treated to prevent additional binding of further biomaterials, the strip would normally be contacted with a material which would shield those portions of the surface which are not bound to the specifically binding biomaterial with a material which prevents attachment of other biomaterials. For example, the strip could be contacted with bovine serum albumin, gelatin, or the like.

The surface would next be contacted with an aqueous solution containing a plurality of particles having particle surfaces having the biological substance associated therewith for a time sufficient for the binding site to bind to the biological substance to thereby bind the particles to the macroextensive surface of the support. This can be accomplished by placing the strip in a solution having the plurality of particles therein and agitating or mildly stirring, if necessary, to make sure that the particles physically contact the macroextensive surface. The biological substance can be associated with the particles by any method, including, for example, physical adsorption, covalent bonding, or the like. Methods of accomplishing such associating are disclosed, for example, in previously mentioned copending application Ser. No. 469,939, filed Feb. 25, 1983, the disclosure of which methods is hereby incorporated herein by reference. Preferably, those portions of the surface of the particles which are not associated with the biological substance will be shielded against attachment of the other biomaterials in the same manner as is the macroextensive surface of the strip. Next, the support or strip is separated from the aqueous sample and rinsed to remove any non-bound particles. At this point the strip can be dried to enhance the ease of observation of the degree of adherence of the particles. The degree of adherence of the particles to the surface is then observed. If no particles adhere, the surface appears clear and unclouded. If particles have adhered to the surface it appears to be quite cloudy. This is particularly easy to observe when the strip is transparent. If the particles are colored, then the resulting coloring of the strip can be observed.

It should be noted that timing and temperature during exposure to the aqueous sample are not critical limitations in the above set out method so long as the time of exposure is sufficiently long for adherence of the biological substance to occur. For example, one hour or more exposure at room temperature is sufficient. Handling is also not a critical limitation since the method is really quite simple to carry out. That is, the method simply requires placing a strip in the suspect urine or other test material and leaving it there for a desired period of time, generally for an hour or more, removing the strip from the suspect urine or other test material, rinsing it, placing the strip in a solution having a plurality of appropriate particles for approximately 10 minutes, removing the strip from such solution, rinsing the strip to remove any non-bound particles, generally drying it, and looking at the strip. The time during which the strip is in the solution with the appropriate particles can be rather critical if false results are to be avoided. Generally, exposure for 9 to 12 minutes has given reproducible and accurate results when an antibody for the HCG has not been previously adsorbed to the strip. If such an antibody has been adsorbed to the strip, the time of exposure to the appropriate particles is not critical in that the minimum exposure time is increased to at least about one hour, but exposure for longer periods of time will not deleteriously effect the test results.

It is desirable in the practice of the invention that the biological substance generally be selected to have an extremely high affinity for the specifically binding biomaterial. This provides very high specificity and sensitivity for the test.

In some instances it may be desirable to initially coat a portion of the surface of the strip with a polysaccharide as taught in copending application Ser. No. 469,939, filed Feb. 25, 1983, the teaching of which is hereby incorporated herein by reference. This helps to prevent undesired biomaterials from attaching to the macroextensive surface. Also, it provides shielding of those portions of the surface which are not bound to the specifically binding biomaterial, the shielding being with a material, the polysaccharide, which prevents attachment of other biomaterials.

In accordance with another aspect of the present invention a kit is provided for carrying out the assay just described. The kit includes a solid support having a water insoluble macroextensive surface capable of associating with the specifically binding biomaterial and with other biomaterials when contacted with an aqueous sample containing the specifically binding biomaterial and other biomaterials for a sufficient period of time. The kit also includes a plurality of particles having particle surfaces bearing the biological substance associated therewith. Such particles would generally be suspended in an aqueous solution. The kit may also contain appropriate rinse solutions, such as phosphate buffered saline, anionic detergent in PBS, and/or solutions for providing shielding of portions of the macroextensive surface. The anionic detergent in PBS serves to reduce false positive test results. The shielding solutions would include, for example, bovine serum albumin, gelatin or the like.

In accordance with yet another aspect of the present invention a method is set out for assaying an aqueous sample by contacting the aqueous sample with a solid support having a water insoluble macroextensive surface already associated with a selected one of the specifically binding biomaterial and the biological substance, the solid support having bound thereto a plurality of particles having particle surfaces associated with a selected other of the specifically binding biomaterial and the biological substance. The particles are bound to the surface via binding of the biological substance to the binding sites. When such a solid support having particles already attached thereto is contacted with the aqueous sample, the particles are released from contact with the surface if the aqueous sample contains a significant amount of either the specifically binding biomaterial or the biological substance. While the theory behind such action is not completely understood it is believed that this may be due to competitive reaction by the dissolved specifically binding biomaterial or biological substance in the aqueous sample for the binding site. In any event, what is observed is the release of the particles from the macroextensive surface. This is an extremely straightforward and simple test and is very easy to run. For pregnancy testing, for example, one need only place a plastic strip having a plurality of particles attached to it into the urine of the suspected pregnant woman and observe whether the particles are released from the surface. This takes only a few minutes, generally about ten minutes, although it may be desirable to run the test somewhat longer for certainty. Generally, the strip would be removed from the urine and rinsed to observed whether or not the particles are washed off. The particles can be of the same nature as the particles discussed for the previous method. That is, they may be made of the same materials, may include a color imparting agent, if desired, may be of a selected size to increase the amount of clouding seen on the strip prior to its insertion in the aqueous sample, etc. Similarly, the strip may be of any of the materials previously disclosed for the strip utilized in the first method discussed above.

Also in accordance with the present invention there is provided a kit which simply comprises a solid support having a water insoluble macroextensive surface associated with a selected one of the specifically binding biomaterial and the biological substance, the solid support having bound thereto a plurality of particles having particle surfaces associated with a selected other of the specifically binding biomaterial and the biological substance, the binding of the particles to the surface being via binding of the biological substance to the binding sites. For comparison purposes it may be desirable to provide two such strips with only one of the two strips being inserted in the suspect pregnancy urine and the other strip being inserted in, for example, male urine. However, the test is so clear that this is not believed to be normally necessary. Appropriate rinsing solution may also form a part of this kit.

In all of the embodiments previously described it is possible, and in some instances may be desirable, to have an intermediate specifically binding biomaterial bound as a bridge to the macroextensive surface and/or the particle surfaces and to, respectively, the specifically binding biomaterial and the biological substance. For example, the macroextensive surface can have a first antigen bound to it while the biological substance can be a second antigen. In this instance, the specifically binding biomaterial can have a first site which is a specific binding partner to the first antigen (allowing the specifically binding biomaterial to be bound via the first antigen to the macroextensive surface) and a second site which is the binding site to the biological substance (the second antigen). It is necessary in such instances that the intermediate specifically binding biomaterial not significantly interfere with binding of the binding site to the biological substances.

The invention will be better understood by reference to the following illustrative examples.

EXAMPLE I

Identical strips of polyvinylchloride plastic approximately 5 millimeters by approximately 40 millimeters and approximately ½ millimeter thick were placed into respective containers and positioned so that approximately 20% of their lengths were beneath the surfaces of respective urine samples, 3 of which were obtained from women who were pregnant and 1 of which was obtained from a non-pregnant woman. The samples were then allowed to stand without being disturbed for approximately one hour. The strips were then removed from the urine samples and rinsed with a phosphate buffered saline (PBS) solution containing 1% bovine serum albumin (BSA) and 0.1% azide.

The strips were next placed into aliquots of a reagent solution containing carboxylated polystyrene particles (MX Covaspheres ®, registered trademark of Covalent Technology Corporation Lot #11J-82, 0.7 micron, fluorescent green) onto which a monoclonal antibody to hCG (10 mg/ml in ascites $k_a=3.3\times10^{10}$) had been adsorbed. The carboxylated polystyrene particles were associated with the monoclonal antibody by contacting 0.2 ml of a 1.05% suspension of the MX Covaspheres ® with 0.05 ml of the monoclonal antibody to β-hCG and 0.1 ml phosphate buffered saline (pH 7.4, made with concentrations of 6.8 gms/l NaCl, 1.48 gms/l $Na_2HPO_4$, 0.43 gm/l $KH_2CO_3$ and containing 0.1% sodium azide) and incubating at room temperature for 1 hour. The particles were then centrifuged down, resuspended by sonication in 0.2 ml PBS containing 1% BSA, and recentrifuged. The washing was repeated two more times. (It has since been found that vortexing works better than sonication). The particles were then resuspended in 0.2 ml PBS containing 1% BSA to provide the reagent solution aliquots. The strips were allowed to stand in the reagent solution aliquots for approximately 10 minutes. The strips were then removed from the reagent solution aliquots and were rinsed with water to remove any non-bound particles. The strips were then dried and it was noted that the previously clear and transparent strips which had been incubated with the urine from pregnant women now exhibited an observable haze indicating a positive test for β-hCG. This constituted a positive test for pregnancy. The strip which had been incubated with the urine from a non-pregnant woman remained clear.

EXAMPLE II

One plastic strip (polyvinylchloride) was incubated for 12 hours in a closed vial containing monoclonal antibody to the α-strand of hCG in a concentration of $1.27\times10^{-2}$ milligrams per milliliter. A second plastic strip (polyvinylchloride) was incubated for 12 hours in a solution containing monoclonal antibody to the β-strand of hCG in a concentration of $1\times10^{-2}$ milligram per milliliter. The rest of the solution was PBS as in Example I. Each strip was washed for fifteen seconds with PBS containing 1% BSA. Each strip was placed in an iodine 125 labelled hCG solution with an iodine activity of 0.9 nanogram per 100,000 cpm in 2% gelatin solution in PBS. The strips were periodically rinsed and counted on a gamma counter. The strip which had been soaked for 12 hours in anti α-hCG showed 488 counts per minutes after 40 minutes. The strip which had been incubated for 12 hours in anti β-hCG showed 449 cpm after 260 minutes. Uncoated strips tested in the same way showed 2325 cpm after 35 minutes. This indicated that the physiadsorption of the hCG on the uncoated plastic strip is about 50 times as effective as binding of the hCG to the strips by means of anti hCG antibodies which have been adsorped onto the strip.

EXAMPLE III

A pair of strips made of polyvinylchloride were both incubated in 50 nanogram per milliliter β-hCG in PBS. As a result, they physiadsorbed the β-hCG. Each strip was rinsed in 1% gelatin in PBS. Each strip was placed in an anti β-hCG microsphere suspension prepared as described in Example I. Each of the strips was then rinsed in PBS. Each of the strips was then stored for 1 hour in PBS. The microspheres remained in adherence with the strips. One of the strips was placed in a sample of male urine for 10 minutes and it was noted that the microspheres remained bound thereto. The second of the strips was placed in a sample of male urine to which 2 nanograms per milliliter of β-hCG had been added. At the end of ten minutes the microspheres had come off of the strip in the second sample of male urine.

This experiment indicates the applicability of a substantially one-step process for determining possible pregnancy through determining the possible occurrence of β-hCG in urine.

EXAMPLE IV

A clear polyvinylchloride strip is incubated with antibody No. 1, then coated with gelatin or BSA. It is then placed in a suspect pregnancy urine and incubated for between 1 and 60 minutes, after which the strip is incubated in microspheres which are coupled to antibody No. 2. These microspheres are carboxylated polystyrene which have been activated with carbodiimide, washed, reacted with antibody No. 2, washed, and reacted with AECM Ficoll. Antibody No. 1 and antibody No. 2 are antibodies which have the property of being able to simultaneously react with human chorionic gonadotrophin or with the β-subunit of human chorionic gonadotrophin, i.e, a given molecule of human chorionic gonadotrophin or β-subunit of human chorionic gonadotrophin can have both antibody No. 1 and antibody No. 2 attached to it simultaneously. After the strip has been incubated in the microspheres for between 1 and 60 minutes, it is removed, rinsed and dried. A positive test is indicated by the plastic strip having a cloudy appearance caused by adherence of the microspheres.

This assay is also applicable for chorionic gonadotrophin in the urine of species other than humans. gonadotrophin in the urine of species other than humans.

EXAMPLE V

Polyvinyl chloride strips were allowed to sit for 12 hours with the lower ends of the strips immersed in a solution containing PBS (previously described in Example I) and an antibody to β-hCG. The concentration of the antibody was 0.01 mg/ml. Its binding constant was $3.3\times10^{10}$. The strips with their adsorbed antibody were removed from the solution, rinsed with PBS containing 1% bovine serum albumin, rinsed briefly with distilled water and allowed to dry.

The following day, 0.1 ml aliquots of carboxylated polystyrene particles (CX Covaspheres ® a registered trademark of Covalent Technology Corporation, Lot #11F82-CX, 0.7 micron fluorescent green) were incubated for one hour with 0.1 ml aliquots of non-pregnant female urine, three of which had been doped with 50 ngms/ml β-hCG and three of which served as controls. The incubation took place in small glass (2.0 ml) serum vials to prevent binding of the β-hCG to the plastic of the Eppindorf tubes in which the second stage of the test would be carried out. The samples were transferred to Eppindorf tubes and the antibody-treated strips were placed in the samples.

First, a pair of strips were removed after ten minutes and rinsed with distilled water. Both the control and 50 ngms β-hCG doped samples yielded clear strips (a negative test). Second, a pair of strips were removed after 20 minutes and rinsed with distilled water. These exhibited a clear control strip and a light haze on the β-HCG sample strip. Third, a pair of strips were removed after thirty minutes and rinsed with distilled water. These exhibited a haze on both the control and the β-hCG sample strips.

These results indicate that it is possible to attach the antibody to the polyvinyl chloride strip and adsorb the sample β-hCG onto the polystyrene particles; however, the timing is critical at this stage of development—a time of ten minutes yielding a false negative result and a time of thirty minutes yielding a false positive result. A timing of twenty minutes yielded a visible but not dramatic positive test and a clear negative test.

While the above examples describe the invention in terms of a test for the presence of β-hCG in urine it should be noted that the test is really much broader in applicability. That is, through proper choice of antigen and antibody the test can be used for determining the presence of possible diseases such a typhoid fever, diptheria, other bacterial infections, and other virus infections and the like. Also, the test can be utilized for testing for biological and chemical warfare agents, drinking water contamination, epideminological studies, mass field screening and the presence of ovulation. Other tests are also possible including tests for the presence of drugs, etc.

INDUSTRIAL APPLICABILITY

In accordance with the present invention test kits and methods are provided for analyzing for any of a number of analytes including specifically hCG. The tests are very easy to run and require little or no training for the operator. They are fast and provide great specificity and sensitivity.

Although the foregoing invention has been described in some detail by way of illustration and example for the purposes of clarity and understanding, it should be recognized that certain changes and modifications may be practiced within the scope of the appended claims.

I claim:

1. In a method of assaying an aqueous sample containing a specifically binding biomaterial having a binding site which is a specific binding partner to a biological substance by observation in light including a selected wavelength in the visual range, said specifically binding biomaterial being in association with other biometerials, comprising:

(1) contacting a solid support having a water insoluble macroextensive surface capable of associating with said specifically binding biomaterial with said aqueous sample for a time sufficient for said specifically binding biomaterial to associate with said macroextensive surface;

(2) separating said support from contact with said aqueous sample;

(3) contacting said macroextensive surface with an aqueous solution containing a plurality of particles having particle surfaces bearing said biological substance associated therewith for a time sufficient for said binding site to bind to said biological substance and to thereby bind said particles to said macroextensive surface;

(4) separating said support from said aqueous solution;

(5) rinsing said support to remove any non-bound particles; and (6) observing the degree of adherence of said particles to said macroextensive surface to thereby perform said assay; the improvement comprising attaining increased speed, ease of assaying, specificity and selectivity, wherein said partices are synthetic polymeric particles and said plurality of synthetic particles are substantially spherical having an average diameter which falls within a range of from about 0.2 micron to about 11.1 microns, are of the substantially the same size within said range and have substantially the same selected refractive index, all as calculated by Mie scattering for clear visual observation of said particles when said particles are adhered to said macroextensive surface and are viewed in light including said wavelength.

2. A method as set forth in claim 1, including, after said step (5) rinsing and before said step (6) observing, the added step of:

drying said rinsed support.

3. A method as set forth in claim 1, wherein said particles have an average diameter which falls within a range from about 0.2 to about 2.0 microns if the degree of adherence is observed in air and from about 0.47 micron to about 11.1 microns is the degree of adherence is observed in water.

4. A method as set forth in claim 3, wherein said support is transparent.

5. A method as set forth in claim 1, wherein said particles comprise latex particles.

6. A method as set forth in claim 1, wherein said particles include a color imparting material.

7. A method as set out in claim 1, further including:

shielding those portions of said surface of the support which are not bound to said specifically binding biomaterial with a material which prevents attachment of other biomaterials.

8. A method as set forth in claim 7, wherein said shielding step precedes said contacting step (1).

9. A method as set forth in claim 7, wherein said shielding step follows said separating step (2) and precedes said contacting step (3).

10. A method as set forth in claim 9, wherein said shielding is provided by contacting said surface with a shielding material selected from bovine serum albumin and gelatin.

11. A method as set forth in claim 1, wherein said biological substance is selected to have an extremely high affinity for said specifically binding biomaterial.

12. A method as set forth in claim 1, wherein said support comprises a hydrophobic polymer.

13. A method as set forth in claim 1, wherein said specifically binding biomaterial is hCG or the $\beta$-subunit of hCG and said biological substance is a monoclonal antibody for hCG or the $\beta$-subunit of hCG.

14. A method as set forth in claim 1, wherein said macroextensive surface has an intermediate specifically binding biomaterial bound thereto, said intermediate specifically binding biomaterial having the property of binding to said specifically binding biomaterial and of not significantly interfering with binding of said binding site to said biological substance.

15. A method as set forth in claim 1, wherein said biological substance is associated with said particle surface via binding to an intermediate specifically binding biomaterial having the property of not significantly interferring with binding of said binding site to said biological substance.

16. A method as set forth in claim 2, wherein said particles have an average diameter which falls within a range from about 0.2 micron to about 2.0 microns.

17. A method as set forth in claim 1, wherein said particle size and refractive index are preselected so that said biomaterial can be assayed at levels as low as about 10 nanograms/ml.

18. A method as set forth in claim 1 wherein said visual observing is from within a cone having an angle from an incident light beam, said angle being substantially that corresponding to substantially the optimal detectivity of Mie scattering.

19. A method as set forth in claim 1, wherein said particles are of a size selected to preferentially Mie scatter light of said selected wavelength, which wavelength corresponds to a selected color.

20. A method as set forth in claim 1, wherein said visual observing is by the naked eye.

21. In a method for assaying an aqueous sample containing a quantity of a specifically binding biomaterial having a binding site which is a specific binding partner to a biological substance by observation in light including a selected wavelength in the visual range, said specifically binding biomaterial being in association with other biomaterials, comprising:

contacting said aqueous sample with a solid support having a water insoluble macroextensive surface associated with a selected one of said specifically binding biomaterial and said biological substance, said solid support having bound thereto a plurality of particles having particle surfaces associated with a selected other of said specifically binding biomaterial and said biological substance, the binding of said particles to said surface being via binding of said biological substance to said binding sites; and observing the degree of release of said particles from said macroextensive surface to thereby perform said assay the improvement comprising attaining increased speed, ease of assaying, specificity and selectivity, wherein said particles are synthetic polymeric particles and said plurality of synthetic particles are substantially spherical having an average diameter which falls within a range of from about 0.2 micron to about 11.1 microns, are of the substantially the same size within said range and have substantially the same selected refractive index, all as calculated by Mie scattering for clear visual observation of said particles when said particles are adhered to said macroextensive surface and are viewed in light including said wavelength.

22. A method as set forth in claim 21, wherein said support is transparent.

23. A method as set forth in claim 21, wherein said particles have an average diameter which falls within a range from about 0.2 micron to about 2.0 microns if the degree of release is observed in air and from about 0.47 micron to about 11.1 microns if the degree of release is observed in water.

24. A method as set forth in claim 21, wherein said particles comprise latex particles.

25. A method as set forth in claim 21, wherein said particles include a color imparting material.

26. A method as set forth in claim 21, wherein said biological substance is selected to have an extremely high affinity for said specifically binding biomaterial.

27. A method as set forth in claim 21, wherein said support comprises a hydrophobic polymer.

28. A method as set forth in claim 21, wherein said particles comprise a hydrophobic polymer.

29. A method as set forth in claim 21, wherein said specifically binding biomaterial is hCG or the $\beta$-subunit of hCG and said biological substance is a monoclonal antibody for hCG or the $\beta$-subunit of hCG.

30. A method as set forth in claim 21, wherein said macroextensive surface has an intermediate specifically binding biomaterial bound thereto, said intermediate specifically binding biomaterial having the property of binding to said selected one of said specifically binding biomaterial and said biological substance and of not significantly interferring with binding of said binding site to said biological substance.

31. A method as set forth in claim 21, wherein said selected other of said specifically binding biomaterial and said biological substance is associated with said particle surfaces via binding to an intermediate specifically binding biomaterial having the propoerty of not significantly interfering with binding of said binding site to said biological substance.

32. A method as set forth in claim 21 wherein said particle size and refractive index are preselected so that said biomaterial can be assayed at levels as low as about 10 nanograms/ml.

33. A method as set forth in claim 21, wherein said particles are of a size selected to preferentially Mie scatter light of said selected wavelength, which wavelength corresponds to a selected color.

34. A method as set forth in claim 21, wherein said visual observing is by the naked eye.

35. In a kit for assaying an aqueous sample containing a specifically binding biomaterial having a binding site which is a specific binding partner to a biological substance by observation in light including a selectled wavelength in the visual range, said specifically binding biomaterial being in association with other biomaterials, comprising:

a solid support having a water insoluble macroextensive surface capable of associating with said specifically binding biomaterial; and a plurality of particles having particle surfaces bearing said biological substance associated therewith; the improvement comprising attaining increased speed, ease of assaying, specificity and selectivity, wherein said particles are synthetic polymeric particles and said plurality of synthetic particles are substantially spherical having an average diameter which falls within a range of from about 0.2 micron to about 11.1 microns, are of the substantially the same size within said range and have substantially the same selected refractive index, all as calculated by Mie scattering for clear visual observation of said particles when said particles are adhered to said macroextensive surface and are viewed in light including said wavelength.

36. A kit as set forth in claim 35, further including:

a solution for rinsing said support to remove any non-bound particles.

37. A kit as set forth in claim 35, further including:

means for shielding those portions of the macroextensive surface which are not bound to said specifically binding biomaterial with a material which prevents attachment of other biomaterials.

38. A kit as set forth in claim 35, wherein said macroextensive surface has an intermediate specifically binding biomaterial bound thereto, said intermediate specifically binding biomaterial having the property of binding to said specifically binding biomaterial and of not significantly interfering with binding of said binding site to said biological substance.

39. A kit as set forth in claim 35, wherein said biological substance is associated with said particle surfaces via binding to an intermediate specifically binding biomaterial having the property of not significantly interfering with binding of said binding site to said biological substance.

40. In a kit for assaying an aqueous sample containing a specifically binding biomaterial having a binding site which is a specific binding partner to a biological substance by observation in light including a selected wavelength in the visual range, said specifically binding biomaterial being in association with other biomaterials, comprising:

a solid support having a water insoluble macroextensive surface associated with a selected one of said specifically binding biomaterial and said biological substance, said solid support having bound thereto a plurality of particles having particle surfaces associated with a selected other of said specifically binding biomaterial and said biological substance, the binding of said particles to said surface being via binding of said biological substance to said binding sites; the improvement comprising attaining increased speed, ease of assaying, specificity and selectivity, wherein said particles are synthetic polymeric particles and said plurality of synthetic particles are substantially spherical having an average diameter which falls within a range of from about 0.2 micron to about 11.1 microns, are of the substantially the same size within said range and have substantially the same selected refractive index, all as calculated by Mie scattering for clear visual observation of said particles when said particles are adhered to said macroextensive surface and are viewed in light including said wavelength.

41. A kit as set forth in claim 40, further including:

a solution for rinsing said macroextensive surface.

42. A kit as set forth in claim 40, wherein said macroextensive surface has an intermediate specifically binding biomaterial bound thereto, said intermediate specifically binding biomaterial having the property of binding to said selected one of said specifically binding biomaterial and said biological substance and of not significantly interfering with binding of said binding site to said biological substance.

43. A kit as set forth in claim 40, wherein said selected other of said specifically binding biomaterial and said biological substance is associated with said particle surfaces via binding to an intermediate specifically binding biomaterial having the property of not significantly interfering with binding of said binding site to said biological substance.

44. A kit as set forth in claim 35, wherein said particles have an average diameter which falls within a range from about 0.2 micron to about 2.0 microns and wherein said clear visual observation of said particles is carried out in air.

45. A kit as set forth in claim 40, wherein said particles have an average diameter which falls within a range from about 0.2 micron to about 2.0 microns and wherein said clear visual observation of said particles is carried out in air.

* * * * *